(12) United States Patent
Vélez-Rivera

(10) Patent No.: US 9,381,221 B2
(45) Date of Patent: Jul. 5, 2016

(54) PHYTOCOMPOSITION FOR THE TREATMENT OF PAIN RELATED TO JOINT DISEASES

(76) Inventor: Héctor de Jesús Vélez-Rivera, Jalisco (MX)

( * ) Notice: Subject to any disclaimer, the term of this patent is extended or adjusted under 35 U.S.C. 154(b) by 110 days.

(21) Appl. No.: 14/372,348

(22) PCT Filed: Jan. 16, 2012

(86) PCT No.: PCT/IB2012/000051
§ 371 (c)(1),
(2), (4) Date: Sep. 23, 2014

(87) PCT Pub. No.: WO2013/108056
PCT Pub. Date: Jul. 25, 2013

(65) Prior Publication Data
US 2015/0024075 A1    Jan. 22, 2015

(51) Int. Cl.
*A61K 36/00* (2006.01)
*A61K 36/28* (2006.01)
*A61K 36/9068* (2006.01)
*A61K 36/324* (2006.01)
*A61K 36/53* (2006.01)
*A61K 9/00* (2006.01)

(52) U.S. Cl.
CPC ............... *A61K 36/28* (2013.01); *A61K 9/0014* (2013.01); *A61K 36/324* (2013.01); *A61K 36/53* (2013.01); *A61K 36/9068* (2013.01)

(58) Field of Classification Search
None
See application file for complete search history.

(56) References Cited

U.S. PATENT DOCUMENTS

| | | | | |
|---|---|---|---|---|
| 5,494,668 A | * | 2/1996 | Patwardhan | A61K 36/324 424/756 |
| 5,976,547 A | * | 11/1999 | Archer | A61K 9/0014 424/742 |
| 6,534,086 B1 | | 3/2003 | Krumhar | |
| 6,579,543 B1 | | 6/2003 | McClung | |
| 2006/0070528 A1 | * | 4/2006 | Kim | A23F 5/26 99/279 |
| 2006/0115544 A1 | | 6/2006 | Frank | |
| 2007/0154575 A1 | | 7/2007 | Shimoda et al. | |
| 2011/0212193 A1 | | 9/2011 | Urschel et al. | |

FOREIGN PATENT DOCUMENTS

| | | |
|---|---|---|
| AU | 2009101061 A4 | 2/2010 |
| ES | 2314057 | 3/2009 |
| IT | 1252074 | 5/1995 |
| WO | WO 02/04003 A2 | 1/2002 |
| WO | WO 2007/145655 A1 | 12/2007 |
| WO | WO 2010/068264 A2 | 6/2010 |

OTHER PUBLICATIONS

International Search Report dated Oct. 2, 2012 issued in corresponding International patent application No. PCT/IB2012/000051.
International Preliminary Report on Patentability dated Feb. 10, 2014 issued in corresponding International patent application No. PCT/IB2012/000051.
Mohammad Azam Khan Muheet-e-Azam vol. III (19th century AD), 05( p. No. 04-08), ( Ref.p. No. of publication:80 ), 1887 AD, Matba Nizami, Kanpur, India.†
Bharata Bhaisajya Ratnakara vol. -V, 06 (p. No. 09-14), ( Ref.p. No. of publication:8 1 ), Edn. 2nd. Reprint. Aug. 1999. ( 20th century), B. Jain Publishers, New Delhi, India.†
Mohammad Akmal Khan, Qaraabaadeen Azam wa Akmal (20th century AD), 04 (p. No. 15-18), ( Ref.p. No. of publication:589 ), 1909 AD, Matba Siddiqi Delhi/Matba Mustafai, Delhi, India.†

\* cited by examiner
† cited by third party

*Primary Examiner* — Qiuwen Mi
(74) *Attorney, Agent, or Firm* — Ostrolenk Faber LLP

(57) ABSTRACT

It is disclosed a phytocomposition which includes: (a) 0.01 wt % to 26 wt % of *Arnica montana* extract; (b) 0.01 wt % to 26 wt % of *Rosmarinus officinalis* extract; (c) 0.01 wt % to 26 wt % of *Zingiber officinale* extract; and (d) 0.01 wt % to 26 wt % of *Boswellia serrate* extract. Said phytocomposition can be used in combination with a pharmaceutically acceptable carrier in order to obtain a pharmaceutical composition that can be used for treating muscle, arthritic and rheumatic pain in a patient, caused by joint diseases, in particular rheumatoid arthritis, osteoarthritis, fibromyalgia, gouty arthritis, psoriatic arthritis, lupus and juvenile arthritis.

8 Claims, 1 Drawing Sheet

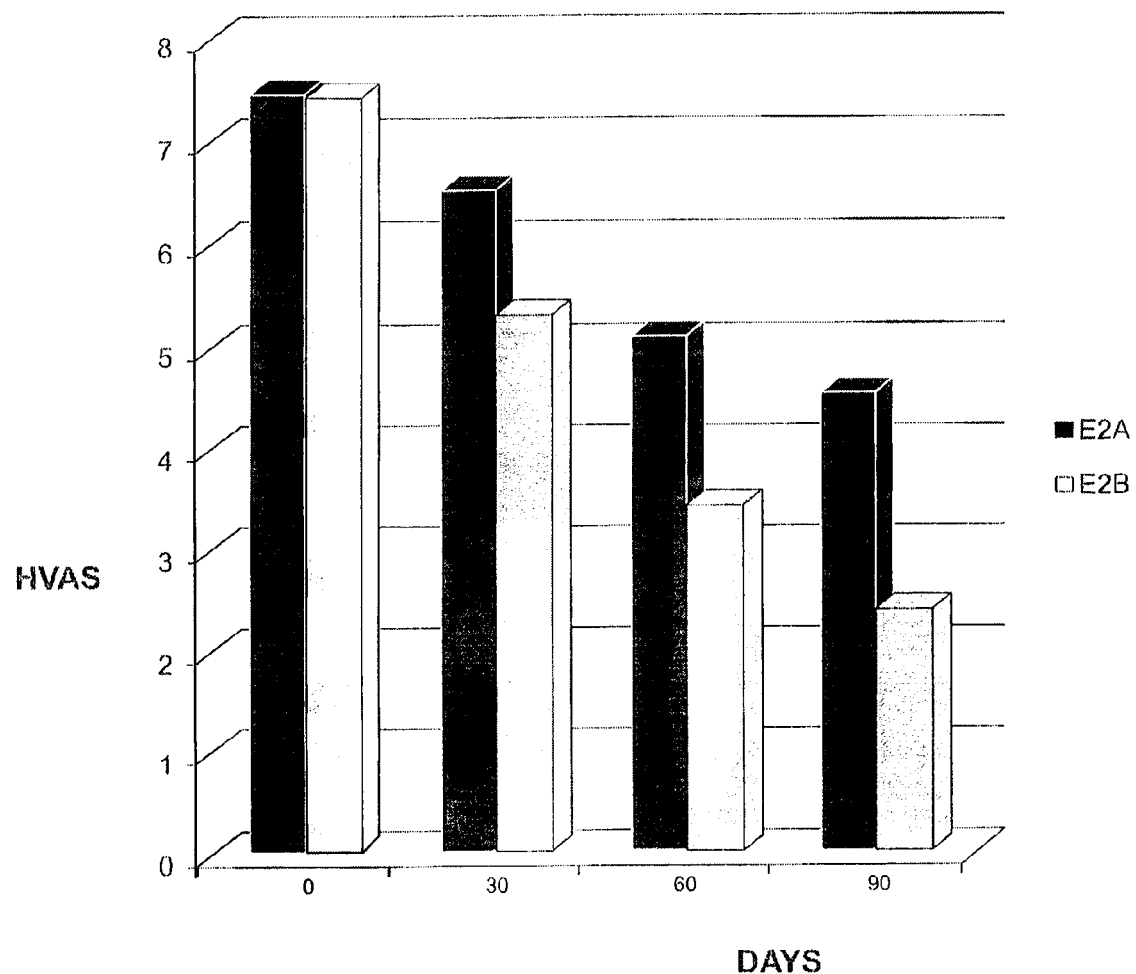

PHYTOCOMPOSITION FOR THE TREATMENT OF PAIN RELATED TO JOINT DISEASES

This application is a national stage application under 35 U.S.C. §371 of International Application No. PCT/IB2012/000051, filed on Jan. 16, 2012.

TECHNICAL FIELD

The instant invention relates to techniques used in the Pharmaceutical Industry for the obtainment and manufacturing of natural drugs, and more particularly, it relates to a phytocomposition for the treatment of pain related to joint diseases.

BACKGROUND OF THE INVENTION

According to the World Health Organization (WHO), it is considered that joint diseases are a major cause of disability in the modern era; in addition such disorders are alarmingly increasing. In the particular case of the United States of America, according to a study conducted in 2010 by the Center for Disease Control and Prevention, approximately 48 million people in this country suffer some joint disease, representing an increase of approximately 3 million people in the last three years. Unfortunately, because of the aging of the population, it is estimated that by the year of 2030 there will be an increase of approximately 40% in the number of people suffering of some type of joint diseases, so that about 67 million people will be affected.

Among the most common joint diseases, one can find rheumatoid arthritis, osteoarthritis, fibromyalgia and gouty arthritis. These diseases are closely related with the presence of pain, which is considered a debilitating symptom of said disease, causing suffering and disability. Chronic or episodic pain is the main cause of loss of function and mobility of joints. In addition to joint pain, other symptoms are inflammation and stiffness of the affected joints.

In general, joint conditions do not cause the death of people. However, it is considered that the greatest impact of these diseases occur in the quality of life of people, causing disability, loss of independence, decreasing in the number of social interactions, distress and decreased well-being of people who suffer this kind of diseases. In this regard, in the United States of America, it is estimated that direct and indirect medical costs associated with these diseases are approximately 128 billion dollars each year.

As it was previously mentioned, the most important joint diseases are rheumatoid arthritis; which is a chronic, recurring and systemic disease that mainly affects diarthrodial joints corresponding to the extremities that have important mobility. Arthritis occurs more frequently in women than in men by a ratio of 3:1, in which the constitutional symptoms include malaise, fever and weight loss.

Most currently treatments that are used to relieve the pain caused by joint diseases have several disadvantages, such as limited effectiveness and the appearance of undesirable side effects.

In the case of conventional treatment for rheumatoid arthritis, the objective is treating the patient in the earliest and most effective possible manner, while having the lowest toxicity. Something similar is done with the person affected by osteoarthritis, but this disease has an evolution time that is longer in comparison with that of rheumatoid arthritis. To do this, there are used the so-called disease modifying drugs (DMARDs) such as gold salts, synthetic antimalarials, the inmunoreductors or immunosuppressive and anti-tumor necrosis factor (TNF) inhibitors and interleukin (IL) biological products. However, the uses of these drugs also cause adverse side effects in the patient, or are too expensive. For example, gold salts cause dermatitis and stomatitis, besides they have a metallic taste; while antimalarials cause razor burn, leucopenia, and peripheral neuropathy, among other adverse effects.

On the other hand, the biological agents, such as chimeric monoclonal antibodies and recombinant fusion proteins are used to increase production of anti-inflammatory cytokines or to inhibit proinflammatory cytokines, have a very good activity and low toxicity; nevertheless, their main disadvantage is that they have a significantly high cost.

In brief words, although there have been significant advances in the understanding and treatment of joint diseases, particularly rheumatoid arthritis, it is not expected a cure for these diseases in the near future, consequently patients will continue suffering the effects of the disease, in which pain is a main symptom.

From the above, nowadays there is a continuous search for alternative drugs that effectively help in the treatment of joint diseases, such as the use of phytodrugs or medicaments comprising extracts of various plant species as their components.

Among those plant species that have been used to relieve various types of pain due to its components, it can be mentioned *Arnica montana* (arnica), *Rosmarinus officinalis* (rosemary), *Zingiber officinale* (ginger) and *Boswellia serrata* (boswellia).

The rnica plant is a perennial herbaceous species belonging to the family Compositae. Arnica is useful in relieving all kind of contusions and bruises as well as muscular and rheumatic pain, among other uses. This plant has a moderate toxicity, so its use is only recommended in an external manner. Within its chemical composition, it can be mentioned flavonoids (astragaloside, isoquercitroside and quercetin-3-gluco-galacturonic aid); carotenes (zeaxanthin); essential oils (caffeic, chlorogenic, thymol, florol, polyacetylenic compounds arnidiol, faradiol, teraxasterol), fixed oils (glycerides of palmitic, oleic and lauric), resins (containing cytisine and gallic acid), alkaloids (arnicina), acetylenic derivatives (betaine and choline), arnicolide A and sesquiterpene lactone (helenalin and dihydrohelenalin), and other compounds.

Among said compounds, flavonoids exert antispasmodic and hypotensive properties. Carotenoids and manganese provides antineuralgic, antirheumatic, anti-inflammatory and anti-echimotic effects. While essential oils have antibacterial and nervous sedative results. It is known that sesquiterpene lactones have anti-inflammatory effects, especially those with α-methylene-φ-lactonic structure. The biological effects of these substances are mediated by immune processes. The most active of these substances is helenalin, to which the use of arnica for pain and inflammation is due.

On the other hand, the prior art has reported that rosemary presents analgesic properties acting against migraine and headaches; muscle, back, hips and bones pain, bruises, rheumatism and inflammation of joints, rosemary has been used as an antispasmodic and has healing properties, among others properties. Rosemary has, in its chemical composition, the presence of flavonoids (hesperidoside, cirsimarine, diosmine, apigenine, luteolin), diterpenic derivatives (rosmaridiphenol, carnosol, carnosic acid; rosmanol, rosmadial, ursolic acid and amyrin), essential oils (cineol, camphene, camphor, borneol), phenolic acids (rosmarinic, caffeic, chlorogenic acid), alkaloids (rosmaricine) and minerals (sodium, potassium, calcium, magnesium, iron, copper, zinc and manganese) among other components.

Likewise, some studies indicate that rosmarinic acid inhibits lipooxygenase activity in the cascade mechanism of arachidonic acid, so that the anti-inflammatory effects of rosemary may be due to the diminished formation of prostaglandins and leukotrienes and induction of D-galactosamine, consequently the formation of peroxynitrite is inhibited which provokes said anti-inflammatory effect.

On the other hand, the active compounds of ginger exhibit activity on the biosynthesis of prostaglandins, besides this plant have effects on arachidonate 5-lipoxygenase that synthesizes leukotrienes. In vitro studies have shown that a ginger extract inhibits the activity of cyclooxygenase and lipoxygenase in the cascade mechanism of the arachidonic acid; it is considered that their anti-inflammatory effects may be due to a diminished formation of prostaglandins and leukotrienes. Ginger also acts as a potent inhibitor of thromboxane synthetase, raising levels of prostacyclin and increasing E2 and F2a prostaglandin. Among the components presents in the ginger extract, it could be mentioned (6)-shogaol which inhibits carrageenan-induced rat paw edema due to cyclooxygenase activity inhibition, while gingerol has an inhibitory effect on the biosynthesis of prostaglandins as PG2, which is involved in inflammatory processes.

Finally, boswellia has analgesic and anti-inflammatory effects similar to non-steroidal anti-inflammatory drugs (NSAIDs). The anti-inflammatory effect of boswellia's resin is attributed to the presence of boswellic acids that inhibit two proinflammatory enzymes, namely, 5-lipoxygenase and human leukocyte elastase (HLE). Boswellic acids increase blood flow to the joints and restore the integrity of the vessels obstructed by spasms; boswellia constitutes an appropriate therapy in cases of stiffness, pain and decreased strength of joints caused by arthritis.

In addition, in the prior art, there are disclosed compositions including among their components any of the plant species above mentioned, but they are combined with other plants. For example, U.S. Pat. No. 5,494,668 describes a composition comprising extracts of *Withania somnifera, Boswellia serrata, Curcuma longa* and *Zingiber officinale*; this composition is preferably for enteral administration and is useful in treating rheumatoid arthritis and osteoarthritis.

Furthermore, U.S. Pat. No. 6,534,086 discloses a composition for the treatment of pain and inflammation caused by joint diseases, among other conditions, the composition consists of a boswellic acid and a curcuminoid, and may further contain other compounds such as gingerol preferably derived from a botanical source.

It is further cited U.S. Pat. No 7,923,038, which discloses a composition for topical application to treat joint conditions, the composition is formulated in a water-based gel without alcohol, this composition comprises various herbal extracts, including arnica and rosemary, which in this specific case, is used to repair tendons, ligaments and damaged soft tissues.

Finally, international publication No. WO2010/068264 describes a formulation for oral administration comprising herbal extracts of *Withania somnifera, Boswellia serrata, Curcuma longa* and *Zingiber officinale*. This formulation is used to alleviate symptoms associated with cyclooxygenase, pro-inflammatory cytokines or pro-inflammatory enzyme conditions, including rheumatoid arthritis and osteoarthritis.

As it can be observed, in the prior art there are various herbal preparations used to treat joint diseases and symptoms associated therewith. Nevertheless, none of said preparation discloses or suggests a synergistic composition as that of the present invention to be used to treat muscle, arthritic and rheumatic pain associated with joint diseases, the composition being effective and of low cost as well as it lacks of those adverse side effects associated with allopathic drugs.

OBJECTS OF THE INVENTION

Having in mind the drawbacks of the prior art, an object of the present invention is to provide a highly effective phytocomposition to significantly reduce pain associated with joint diseases, particularly muscle, arthritic and rheumatic pain in patients who suffer those diseases.

A further object of the present invention is to provide a safe and effective pharmaceutical composition including the phytocomposition and a pharmaceutically acceptable carrier, the pharmaceutical composition being topically administered.

It is also another object of the present invention, the use of a pharmaceutical composition including the phytocomposition and a pharmaceutically acceptable carrier to significantly reduce pain associated to joint diseases in patients who suffer said diseases by administering a safe and effective therapeutically amount of said pharmaceutical composition.

Still a further object of the present invention is to provide a pharmaceutical composition comprising the phytocomposition and a pharmaceutically acceptable carrier, the pharmaceutical composition lacking of side effects.

It is further another object of the present invention to provide a pharmaceutical composition comprising the phytocomposition and a pharmaceutically acceptable carrier, which preparation method saves costs compared to traditional allopathic medicaments that are used to decrease pain associated with joint diseases.

SUMMARY OF THE INVENTION

To this end, it has been developed a phytocomposition comprising: (a) extract of *Arnica montana*; (b) extract of *Rosmarinus officinalis*; (c) extract of *Zingiber officinale*; and (d) extract of *Boswellia serrata*. In a preferred embodiment of the invention, the phytocomposition comprises:

(a) from 0.01% to 26%, by weight of the total weight, of an extract of *Arnica montana;*

(b) from 0.01% to 26%, by weight of the total weight, of an extract of *Rosmarinus officinalis;*

(c) from 0.01% to 26%, by weight of the total weight, of an extract of *Zingiber officinale*; and, (d) from 0.01% to 26%, by weight of the total weight, of an extract of *Boswellia serrata*.

Other aspects of the present invention are related to a pharmaceutical composition comprising the phytocomposition as above defined in combination with a pharmaceutically acceptable carrier, which is preferably administered topically as a lotion, emulsion, cream or gel. This composition is used to treat muscle, arthritic and rheumatic pain caused by joint diseases in a patient.

BRIEF DESCRIPTION OF THE DRAWINGS

The novel features that are considered characteristic of this invention are set forth with particularity in the appended claims. However, some embodiments, features and objects and advantages of the invention, will be best understood from the detailed description, when read in conjunction with the accompanying drawing, in which:

FIG. 1 is a bar graph, in which, there are illustrated the results in reduction of pain of two groups of patients with joint diseases, in which one group was treated with a phytocomposition containing only two plant extracts and the other group was treated with the pharmaceutical composition of the present invention.

DETAILED DESCRIPTION OF A PREFERRED EMBODIMENT OF THE INVENTION

As it was described in the background section of the invention, in the world, there are a large number of patients suffering from joint diseases that incapacitate them, so that there are not able to continue with their work activities, even they are not able to perform their normal activities of daily living, deteriorating their quality of life.

Although, there are currently several medicaments in traditional or allopathic medicine used for the treatment of pain caused by joint diseases, they do not significantly reduce pain; moreover the medicaments are expensive and have serious side effects.

Due to the above, it has been developed a phytocomposition having a synergistic effect when used in the treatment to reduce muscle, arthritic and rheumatic pain associated with joint diseases, since the phytocomposition provides analgesic effects, allowing the patient to effectively decrease pain. This phytocomposition was developed using extracts of *Arnica montana* (arnica), *Rosmarinus officinalis* (rosemary), *Zingiber officinale* (ginger) and *Boswellia serrata* (boswellia).

Also, it was developed a pharmaceutical composition comprising said phytocomposition and a pharmaceutically acceptable carrier, which is administered topically to patients suffering from pain caused by joint diseases. Moreover, it is disclosed the use of a therapeutically effective amount of said pharmaceutical composition to significantly reduce pain caused by joint diseases. It should be understood that, as described herein, a "therapeutically effective amount" refers to an amount necessary to achieve a selected result.

It is worth mentioning that various preferred embodiments of the phytocomposition of the instant invention are disclosed; however, the scope of the invention should not be limited to these disclosed embodiments or examples; since they can vary significantly without departing from the inventive concept claimed in the present invention.

In this context, it is disclosed a particularly specific embodiment of the present invention useful in the treatment of muscle, arthritic and rheumatic pain, which comprises:
(a) from 0.01% to 26%, by weight of the total weight, of an extract of *Arnica montana;*
(b) from 0.01% to 26%, by weight of the total weight, of an extract of *Rosmarinus officinalis;*
(c) from 0.01% to 26%, by weight of the total weight, of an extract of *Zingiber officinale*; and, (d) from 0.01% to 26%, by weight of the total weight, of an extract of *Boswellia serrata.*

In a preferred embodiment of the present invention, the phytocomposition comprises:
(a) from 0.01% to 15%, by weight of the total weight, of the extract of *Arnica montana;*
(b) from 0.01% to 15%, by weight of the total weight, of the extract of *Rosmarinus officinalis;*
(c) from 0.01% to 15%, by weight of the total weight, of the extract of *Zingiber officinale*; and,
(d) from 0.01% to 15%, by weight of the total weight, of the extract of *Boswellia serrata.*

More preferably, the phytocomposition of the present invention comprises:
(a) from 8% to 12%, by weight of the total weight, of the extract of *Arnica montana;*
(b) from 8% to 12%, by weight of the total weight, of the extract of *Rosmarinus officinalis;*
(c) from 8% to 12%, by weight of the total weight, of *Zingiber officinale*; and.
(d) from 8% to 12%, by weight of the total weight, of the extract of *Boswellia serrata.*

Regarding the species *Arnica montana*, it is worth mentioning that the flowers are the useful part of the plant to obtain the extract; with respect to the plant *Rosmarinus officinalis* the useful portion is the whole plant once chopped; while the useful part of the plant for obtaining the extract of *Zingiber officinale* is the root or rhizome; and in the case of the *Boswellia serrata*, the resin extracted from the bark is used.

The extracts of these four species of the phytocomposition of the present invention are selected from the group of alcoholic extracts, aqueous extracts or hydro-alcoholic extracts. In the specific embodiment of the present invention, there are used preferably hydro-alcoholic extracts, that is to say, they are prepared from a mixture of water and an alcohol, wherein said extracts are obtained through several methods well known in the prior art.

On the other hand, as it was above mentioned, in order to administrate the previously defined phytocomposition to a patient, there is provided a pharmaceutical composition comprising a therapeutically effective amount of said phytocomposition in combination with a pharmaceutically acceptable carrier, the pharmaceutical composition is preferably topically administered.

The pharmaceutical composition is formulated in a form selected from a lotion, an emulsion, a cream or a gel, more preferably it is formulated as a lotion.

Thus, the phytocomposition of the present invention in combination with a pharmaceutically acceptable carrier allows preparing the pharmaceutical composition that is useful in the treatment of muscle, arthritic and rheumatic pain caused by joint diseases in mammals, particularly in humans, said joint diseases being rheumatoid arthritis, osteoarthritis, fibromyalgia, gouty arthritis, psoriatic arthritis, lupus and juvenile arthritis.

The pharmaceutical composition provides analgesic and anti-inflammatory effects, in addition, it allows reducing the dysfunction of the joints improving joint mobility, and in this regard, dysfunction is characteristically present in people with joint diseases.

As it was previously disclosed, the pharmaceutical composition is used in patients with joint diseases, wherein the treatment comprises administering to a patient, preferably topically, a therapeutically effective amount of a pharmaceutical composition comprising the phytocomposition of the instant invention as above defined. In this concern, those joint diseases, where the composition can be used, are those previously mentioned.

The phytocomposition for treating muscle, arthritic and rheumatic pain, and the pharmaceutical composition that is prepared with said phytocomposition will be more clearly illustrated by the examples described below, which are presented for illustration purposes, but they are not limiting the invention, said examples are the following:

Example 1

Preparation of the Phytocomposition in a Pharmaceutical Form of a Lotion

Identification and weighing of *Arnica montana* extract, *Rosmarinus officinalis, Zingiber officinale* and *Boswellia serrata* was carried out. The extracts once weighted were filtered through a stainless steel mesh of 80 microns and placed in a stainless steel tank of adequate capacity. Subsequently, water and alcohol were added and the pharmaceutically acceptable carrier, in addition an herbal essence was also added; The tank contents were stirred by a stirrer-propeller system at 600 rpm for 20 minutes.

Once the time finished, the solution was allowed to stand for 5 minutes to finally obtain a lotion that embodies the phytocomposition of the present invention.

Example 2

Clinical Trial

A randomized double-blind study with two parallel groups was conducted at the Centre for Rheumatic Diseases Artricenter® located in Mexico City. For this trial, a total of 100 people were involved, of which 52 were men and 48 were women, who had been diagnosed with rheumatoid arthritis in hands. These 100 people were subjected to a clinical study in order to observe the effects and benefits of using the pharmaceutical composition of the instant invention in a dosage form of a lotion compared with a phytocomposition containing only two herbal extracts.

Pain was measured at the beginning, during and after the treatment, using the horizontal visual analog scale (HVAS) from 0 to 10.

The main inclusion criteria for the trial were: patients aged between 45 and 75 years, male or female, the patient being diagnosed with rheumatoid arthritis in hands and with equal or greater pain 5 in the HVAS scale as mentioned in the last paragraph.

The exclusion criteria were mainly patients with inflammatory disease other than rheumatoid arthritis and those people with steroid injection until two months before entering to the trial.

In addition, those patients who did not attend the control or who abandoned the treatment by own decision were eliminated from the trial.

There were randomly assigned 50 patients to each group. Each patient of the first group (example E2A) received a 65 ml container with a lotion of the phytocomposition comprising extract of *Arnica montana* and extract of *Rosmarinus officinalis* and excipient to complete 100 ml. On the other hand, each patient in the second group (example E2B) received a 65 mL container with a lotion of the phytocomposition of the present invention, which was prepared as described in Example 1.

In both cases, the lotion was applied topically four times a day, every 6 hours for 90 days. Of all the patients, 100% completed the treatment.

In FIG. 1 it can be seen that, at the time of starting treatment, patients in both groups had similar pain on the HVAS scale (7.48 for E2A to 7.44 for E2B). At 30 days, it was possible to observe a significant difference in pain reduction of the patients, said reduction was greater in patients that used the composition in the group E2B. This difference became greater when the treatment finished. It was found that, although there was a decrease in pain in the group of patients E2A (4.54 of value on the HVAS) after 90 days of treatment, the pain reduction was greater in patients of the group E2B (2.38 of value on the VAS). That is to say, using a phytocomposition with two plant extracts (E2A) there was a reduction of about 39% in pain, while using the phytocomposition of the present invention (E2B), pain in patients was reduced about 68%. With this, it is shown that when the combined extracts of *Arnica montana, Rosmarinus officinalis, Zingiber officinale* and *Boswellia serrata* are used in the phytocomposition, a synergistic effect is obtained; showing better results when the phytocomposition is used to decrease muscle, arthritic and rheumatic pain associated with joint diseases. These results could have not been deduced in an obvious manner by a skilled in the art, because, although patients that used a composition containing extracts of arnica and rosemary had a reduction in pain, adding extracts of boswellia and ginger, the effect in pain reduction was more evident as well as there was a reduction in inflammation of the affected joints, which also lead to a reduction in joint stiffness.

It is also important to note that the adverse effects caused by the use of the pharmaceutical composition of the present invention are minimal or absent, particularly when compared with those adverse events caused by the NSAIDs.

On the other hand, it is evident considering that the pharmaceutical composition described in the embodiments of the present invention has a lower cost in comparison with the allopathic drugs used in the treatment of joint diseases.

In accordance to the above disclosed, it will be observed that the phytocomposition for treating muscle, arthritic and rheumatic pain of the present invention, and the pharmaceutical composition prepared with the same, have been conceived to assist in the treatment of joint diseases and more specifically, arthritis; the composition helps to improve dysfunction in patients in an extremely effective manner. It is important to mention that the pharmaceutical composition of the present invention may comprise numerous modifications, such as the concentration of the 4 basic species that form the same, as well as the pharmaceutical formulation to be administered to a patient, among other modifications.

Although, the above description has referred to certain embodiments of the present invention, it should be emphasized that numerous modifications are possible to said embodiments without departing from the scope of the invention. Therefore, the present invention should not be limited except by the prior art as well as by the appended claims.

What is claimed is:

1. A phytocomposition comprising the following weight percentage concentrations of the total weight of the phytocomposition:
    a) from 0.01% to 15% of an extract of *Arnica montana;*
    b) from 0.01% to 15% of an extract of *Rosmarinus officinalis;*
    c) from 0.01% to 15% of an extract of *Zingiber officinale*; and
    d) from 0.01% to 15% of an extract of *Boswellia serrata.*

2. A phytocomposition according to claim 1, wherein the extracts are present in the phytocomposition according to the following weight percentage concentrations of the total weight of the phytocomposition
    a) from 8% to 12% of the extract of *Arnica montana;*
    b) from 8% to 12% of the extract of *Rosmarinus officinalis;*
    c) from 8% to 12% of the extract of *Zingiber officinale*; and,
    d) from 8% to 12% of the extract of *Boswellia serrata.*

3. A phytocomposition according to claim 1, wherein the extracts of *Arnica montana, Rosmarinus officinalis, Zingiber officinale* and *Boswellia serrata*, are selected from the group consisting of aqueous extracts, alcoholic extracts and hydroalcoholic extracts.

4. A phytocomposition according to claim 3, wherein the extracts selected are hydro-alcoholic extracts.

5. A pharmaceutical composition, wherein it comprises a therapeutically effective amount of the phytocomposition as claimed in claim 1 and a pharmaceutically acceptable carrier.

6. A pharmaceutical composition according to claim 5, wherein the pharmaceutical composition is formulated for topical administration.

7. A pharmaceutical composition according to claim 5, wherein the pharmaceutical composition is formulated in the form of a lotion, emulsion, cream or gel.

8. A pharmaceutical composition according to claim 7, wherein the composition is formulated as a lotion.

* * * * *